United States Patent [19]
Hoffman et al.

[11] Patent Number: 6,132,466
[45] Date of Patent: Oct. 17, 2000

[54] TEMPOROMANDIBULAR PROSTHETIC JOINT

[76] Inventors: David C. Hoffman, 25 Alexa Pl., Red Bank, N.J. 07701; Michael J. Pappas, 61 Gould Pl., Caldwell, N.J. 07006

[21] Appl. No.: 09/332,354

[22] Filed: Jun. 11, 1999

Related U.S. Application Data

[63] Continuation-in-part of application No. 08/850,997, May 5, 1997, abandoned.
[60] Provisional application No. 60/016,342, May 3, 1996.
[51] Int. Cl.[7] ........................................................ A61F 2/30
[52] U.S. Cl. ........................................................ 623/17.17
[58] Field of Search .............................. 623/17.17, 23.39, 623/18.11

[56] References Cited

U.S. PATENT DOCUMENTS 5,405,393  4/1995  Falkenstom ........................... 623/17.17
5,549,680  8/1996  Gordon ................................. 623/17.17

*Primary Examiner*—David J. Isabella
*Attorney, Agent, or Firm*—Anthony J. Casella; Gerald E. Hespos; Michael J. Porco

[57] ABSTRACT

A temporomandibular joint prosthesis is provided. The prosthesis includes the condyle component for attachment to the ramus of a temporomandibular joint to replace the natural condylar head. The condyle component is attached to the natural ramus by a fixation system that may include plasma-sprayed pegs or plasma-sprayed double screws. The prosthesis further includes a fossa component assembly having a metallic bone attachment member and a plastic bearing. The plastic bearing is disposed and configured for articular bearing engagement with the condyle component of the prosthesis.

17 Claims, 3 Drawing Sheets

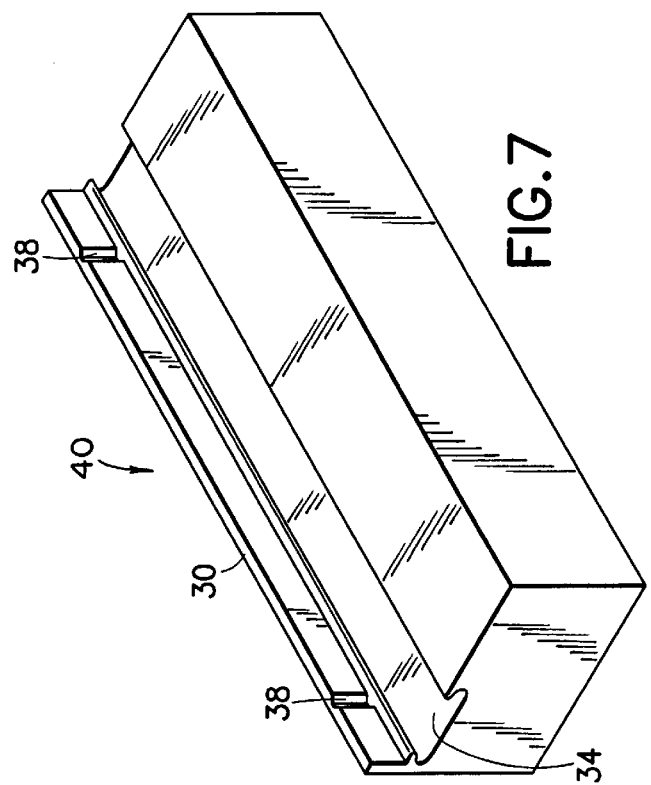
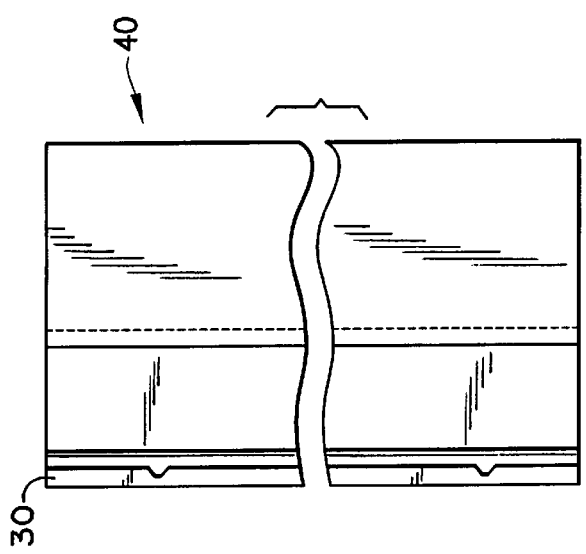
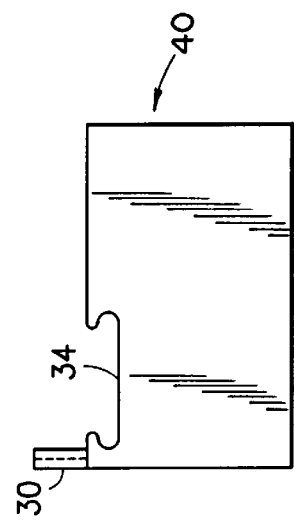

TEMPOROMANDIBULAR PROSTHETIC JOINT

This application is a continuation-in-part of application Ser. No. 08/850,997, flied May 5, 1997, now abandoned, which in turn claims priority on Provisional Patent Application Ser. No. 60/016,342 which was filed May 3, 1996.

BACKGROUND OF THE INVENTION

1. Field of the Invention

The subject invention relates to a prosthetic temporomandibular joint.

2. Description of the Related Art

The prior art temporomandibular joint prosthesis includes a condyle component attached to the lower jaw and a fossa component attached to the upper jaw. The condyle components have included a mounting portion in the form of a generally planar support having apertures therethrough for receiving screws. The support is positioned adjacent the ramus and is secured in that position by screws passing through the apertures in the support. A neck extends from the support, and a condyle extends from the neck. The condyle of some prior art temporomandibular joint prostheses is spherical. On other prior art prostheses, the condyle is substantially an ellipsoid that is elongated in a general medial to lateral direction. The fossa component of the prior art temporomandibular joint typically has been in the form of a thin bearing having a superior surface that is mounted to the fossa and an inferior surface that is configured to be congruent with the condyle and that engages the condyle in articular bearing engagement. Examples of such prior art prosthetic temporomandibular joints are shown in U.S. Pat. No. 4,778,472; U.S. Pat. No. 4,936,852 and U.S. Pat. No. 5,445,650.

The prior art temporomandibular joint prosthesis having a high degree of congruency between the condyle and the fossa would be effective if the temporomandibular joint of a jaw were subject to pure pivotal movement about a medial-lateral axis. However, the temporomandibular joint is subject to a very complex and varying array of applied forces during chewing and during other normal facial movements. In particular, moments may be applied to the temporomandibular joint about an anterior-posterior axis and about a superior-inferior axis. Furthermore, anterior-posterior loads and medial-lateral loads may be applied to the condyle relative to the fossa component. In view of the complexity of these forces and moments, and in view of the relatively high loads, prior art temporomandibular joint prostheses have been subject to dislocation. Furthermore, certain loads applied to the prior art temporomandibular prosthesis may cause sufficient movement of the components to replace the intended congruent contact with a substantially point contact. The single point of contact between prosthetic components necessarily concentrates the applied load to the point of contact, and has led to component failure. Failure is particularly likely to occur in the articular bearing surface of the fossa component.

In view of the above, it is an object of the subject invention to provide a temporomandibular joint prosthesis that is better able to withstand the complex loads applied to the prosthesis.

SUMMARY OF THE INVENTION

The subject invention is directed to a two-component prosthesis that replaces the temporomandibular joint. The prosthesis comprises a condyle component and a fossa component assembly which are in articular bearing engagement with one another to permit both rotation about at least one axis and translation in at least one direction.

The condyle component of the prosthetic joint attaches to the lateral side of the ramus and replaces the natural condylar head. The condyle component of the prosthesis is formed unitarily from metal, and is secured to the natural bone with a fixation system. The fixation system employs a combination of mechanical and osteointegrated attachments that may use either plasma-sprayed pegs or plasma-sprayed double screws that have an anti-micromovement lock. The condyle component of the prosthesis may be formed from titanium. However, the condylar head of the condyle component may have a titanium nitride layer or a thin layer of ceramic. The condyle may define a surface of revolution generated about a medial-lateral axis. In particular, the surface of revolution may be formed by a relatively flat curve rotated about the medial-lateral axis. Thus, medial and lateral ends of the condyle may be tapered slightly toward the medial-lateral axis.

The fossa component assembly of the prosthesis has a metal bone attachment portion and a thermoplastic bearing portion that may be engaged with one another. The metal portion of the fossa component of the prosthesis may be secured by screws, such as the above described double screws, extending into the natural bone. The thermoplastic bearing portion may be formed from a high molecular weight polyethylene. The thermoplastic portion of the fossa component has an inferior bearing surface with which the condylar head of the condyle component is engaged.

The bearing surface of the fossa component is configured to accommodate rotational movement about the medial-lateral axis, which, as explained above, is a dominant movement in the temporomandibular joint. However, the inferior bearing surface of the fossa component also is configured to accommodate movements in response to the other complex loads applied to the joint. Additionally, the inferior bearing surface is configured to avoid point contact and to maintain line contact and/or an acceptable degree of congruency. In this regard, the inferior bearing surface of the fossa component is substantially linear in medial to lateral directions at all positions thereon. Thus, the condylar head, which is tapered at its medial and lateral extremes, can pivot slightly about an anterior-posterior axis in response to moments applied on the condyle component. The inferior bearing surface of the fossa component includes a region that is substantially congruent with the condylar head in a medial to lateral direction when the condyle is in a position substantially corresponding to the highest loads imposed on the joint. The inferior bearing surface of the fossa component preferably is elongated in a medial to lateral direction to accommodate some medial to the lateral translation of the condylar head relative to the fossa component in response to certain loads imposed on the joint. However, the inferior bearing surface of the fossa component is characterized by lips at anterior and posterior extreme positions to prevent complete dislocation.

BRIEF DESCRIPTION OF THE DRAWINGS

FIG. 7 is a perspective view of a blank for forming the attachment portion of the fossa component.

FIG. 8 is a top plan view of the blank for the attachment portion.

FIG. 9 is an end elevational view of the blank for the attachment portion.

DETAILED DESCRIPTION OF THE PREFERRED EMBODIMENT

Figures 1, 2:
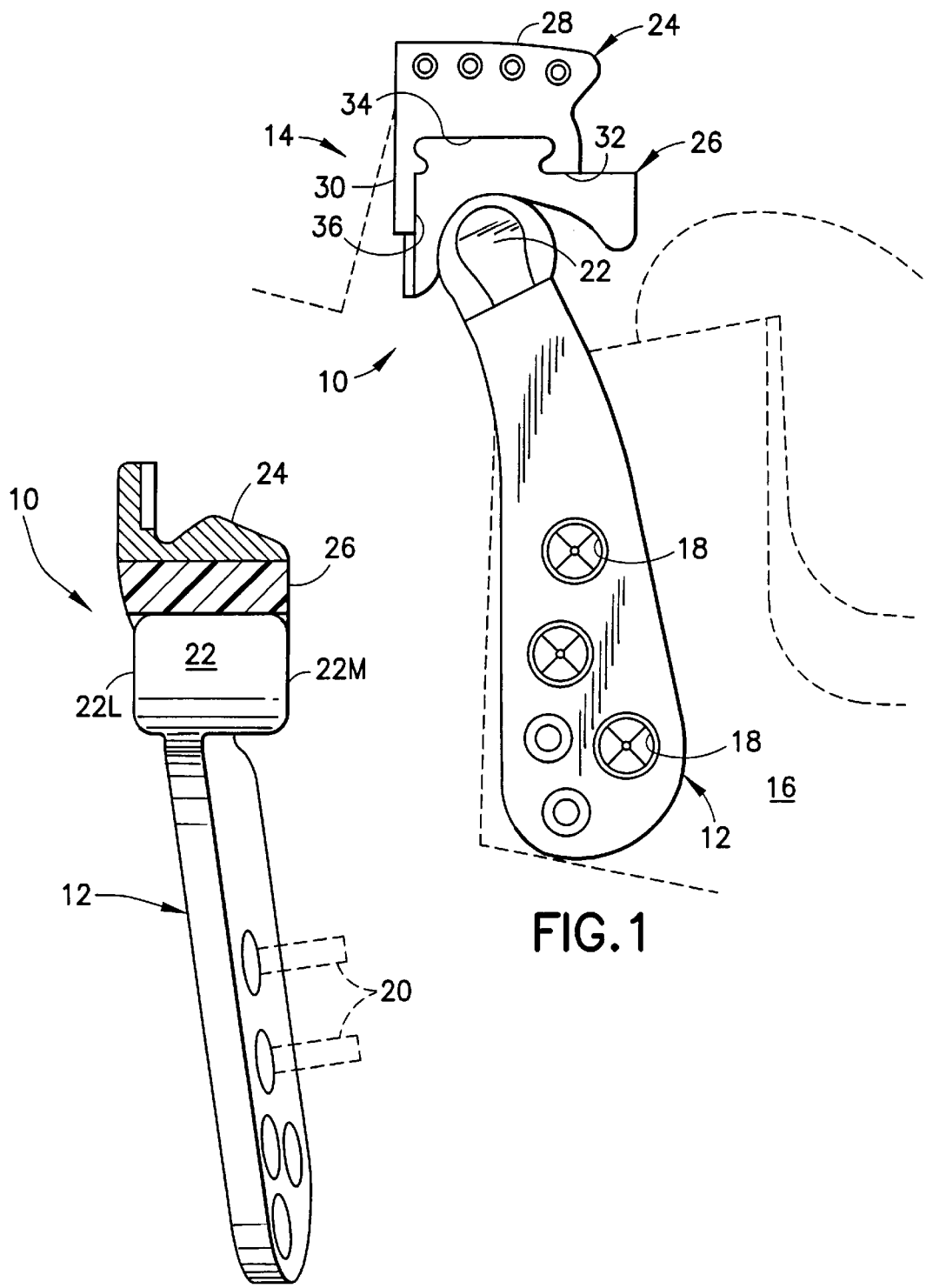
FIG. 1 is a side elevational view of a prosthesis in accordance with the subject invention.
FIG. 2 is a rear elevational view of the prosthesis.
Figure 3:
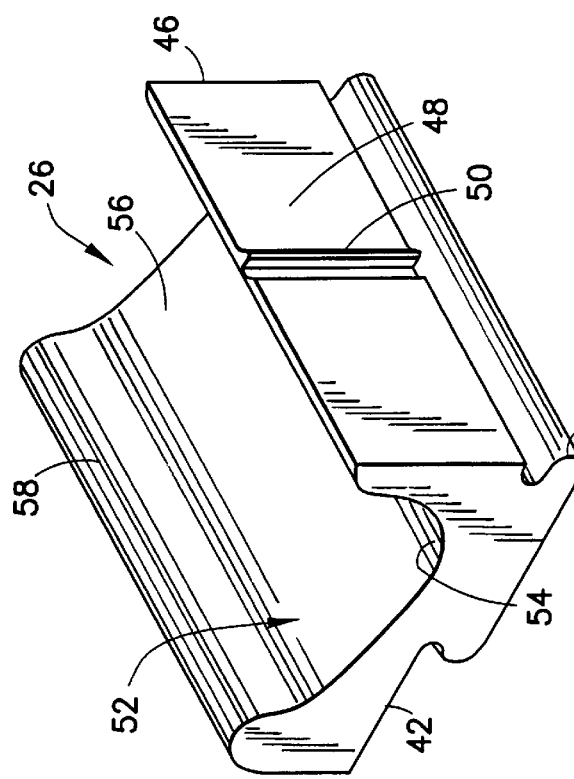
FIG. 3 is a prospective view of a blank for the bearing of the fossa component.
Figure 5:
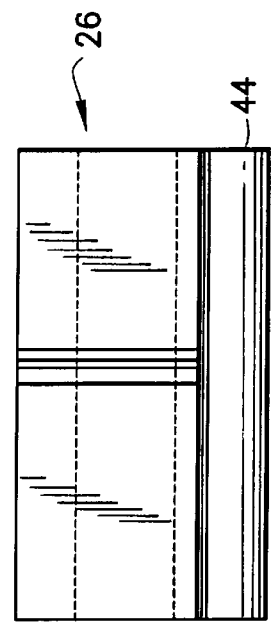
FIG. 5 is a side elevational view of the bearing blank shown in FIGS. 3 and 4.
Figure 4:
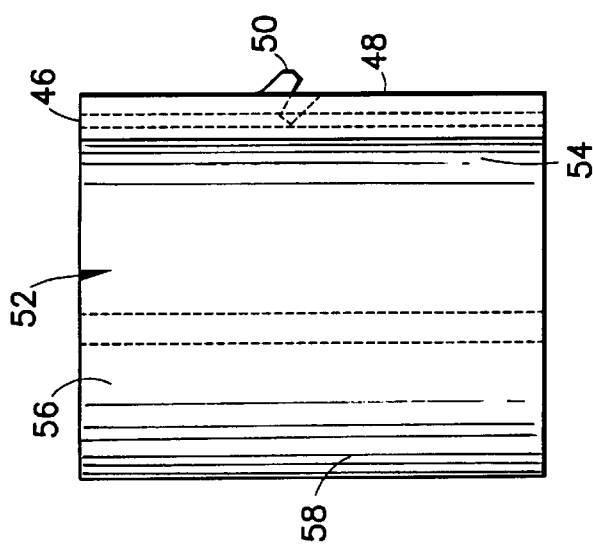
FIG. 4 is a top plan view of the bearing blank shown in FIG. 3.
Figure 6:
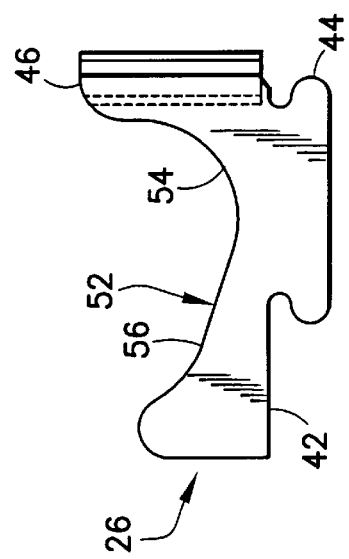
FIG. 6 is an end elevational view of the bearing blank.

A temporomandibular joint prosthesis in accordance with the subject invention is identified generally by the numeral 10 in FIGS. 1 and 2. The prosthesis 10 includes a condyle component 12 and a fossa component assembly 14. The condyle component 12 attaches to the lateral side of the ramus 16 and replaces the natural condylar head of the ramus. The condyle component 12 includes a plurality of apertures 18 extending therethrough. Elongate attachment devices 20 pass through the apertures 18 for securely affixing the condyle component 12 to the ramus 16. The attachment devices 20 may comprise plasma-sprayed pegs or plasma-sprayed double screws that have an anti-micromovement lock. The preferred attachment devices 20 are the above-referenced double screws which comprise an outer screw and an inner screw. The outer screw includes an engagement end having an array of external threads and an actuating end. An internally threaded aperture extends a short distance into the actuating end, and radially aligned slots extend into the actuating end. The radially aligned slots extend entirely from the internally threaded aperture to the outer periphery of the outer screw. An inner screw is threadedly engageable with the internal aperture. The inner screw is operative for generating an outward deflection of portions of the outer screw between the respective slots. This outward deflection effectively tightens the outer screw against surrounding portions of the condyle component and against any adjacent bone stock to which the condyle component is affixed. Thus, the attachment devices 20 are effective to achieve a mechanical and osteointegrated attachment of the condyle component 12 to the ramus 16.

The condyle component 12 includes a condylar head 22 which preferably is a surface of revolution generated about an axis extending in a medial to lateral direction. The surface of revolution may be formed by a relatively flat curve rotated about the medial-lateral axis. Thus, the condylar head 22 tapers toward the axis at the medial and lateral extremes 22M and 22L of the head 22, as shown in FIG. 2. The condyle component 12 may be formed from titanium. However, the condylar head 22 may be coated with a titanium nitride or a thin layer of ceramic.

The fossa component assembly 14 includes a metallic bone attachment portion 24 having a plastic bearing 26 attached hereto. The plastic bearing 26 preferably is formed from a high molecular weight polyethylene and defines the inferior bearing surface against which the condylar head 22 articulates, as explained below.

The metallic bone attachment portion 24 includes a superior wall 28 and a posterior wall 30. The superior wall 28 has an inferior surface 32 with a dovetailed slot 34 extending generally in a medial to lateral direction along the inferior surface 32. The posterior wall 30 disposed posteriorly of the dovetailed slot and extending inferiorly therefrom. The posterior wall 30 includes an anterior face 36 that will provide support for a portion of the plastic bearing 26 as explained further herein. The anterior face 36 is formed with an inferior-to-posterior groove 38 approximately midway between the medial and lateral ends of the bone attachment portion.

The metallic bone attachment portion 24 is formed from an elongate bland 40 that is shown in FIGS. 7–9. The blank 40 is machined to include the dovetail slot 34 and the posterior wall 30. The blank 34 is cut and further machined to define a superior surface for nesting against the fossa as shown in FIGS. 1 and 2 above.

The plastic bearing 26 includes a superior wall 42 having a surface 42 configured for bearing engagement against the inferior surface 32 of the metallic bone attachment portion 24. The superior surface 42 of the plastic bearing 26 includes a dovetail projection 44 that extends generally in a medial-to-lateral direction and that is dimensioned for close sliding engagement in the dovetail slot 34 of the metallic bone attachment portion 24. The plastic bearing 26 further includes a posterior wall 46 with a posterior face 48 dimensioned and configured for bearing engagement against the anterior face 36 of the posterior wall 30 of the metallic bone attachment portion 24. The posterior face 48 includes a deflectable locking ridge 50 which is disposed and configured for locked engagement in the groove 38 of the bone attachment portion 24. The dovetail projection 44 of the plastic bearing 26 can be slid into the dovetail slot 34 of the metallic bone attachment portion 24. After sufficient movement, the locking ridge 50 of the plastic bearing 26 will engage in the locking groove 38 on the metallic bone attachment portion 24.

The plastic bearing 26 further includes an inferior bearing surface identified generally by the numeral 52 in FIGS. 6–9. The inferior surface 52 extends continuously from a medial side 24M to a lateral side 24L of the plastic bearing 26. The inferior bearing surface 52 is configured to be substantially linear in a medial-to-lateral direction at any anterior to posterior position on the inferior bearing surface 52. However, the inferior bearing surface 52 is concavely arcuate in an anterior-posterior direction. The concave configuration of the bearing surface 52 includes a generally cylindrical region 52 generated about a medial to lateral axis and disposed at the intersection of superior wall 42 and the posterior wall 46. The cylindrically concave portion 54 of the interior bearing face 52 is dimensioned to substantially congruently nest with a central portion of the condylar head 22 between the medial and lateral extremes when the condylar head 22 is in a position corresponding substantially to a maximum applied load. The posterior wall 46 of the plastic bearing 26 permits a slight inferior movement of the condylar head 22 relative to the plastic bearing 26 from the position of maximum load shown in FIGS. 1 and 2. However, the posterior wall 46 of the plastic bearing 26 prevents posterior dislocation of the condylar head 22. The inferior bearing surface 52 further includes a substantially planar section 56 extending tangentially anteriorly from the cylindrical section. The planar section 56 of the inferior bearing surface 52 permits a sliding anterior-posterior translation of the condylar head 22 relative to the inferior bearing surface 52. However, the plastic bearing 26 is further provided with an anterior lip 58 that substantially prevents dislocation of the condylar head 22 in an anterior direction.

The prosthesis 10 offers several advantages over the prior art. In particular, the medial to lateral linear configuration of the inferior bearing surface 52 and the slightly tapered configuration of the condylar head 22 near the medial and lateral ends provide at least a line contact for all relative positions of the condylar head 22 on the bearing surface 52.

However, the slight taper of the condylar head 22 near the medial and lateral extremes 22M and 22L enable a slight pivoting movement of the condyle component 12 about an anterior-posterior axis in response to applied loads. Additionally, during the maximum loading conditions shown in FIG. 1, the arcuate section 52 of the bearing surface 50 provides a high degree of congruency in an anterior to posterior direction with the condylar head 22. This anterior-posterior congruency, combined with the medial to lateral congruency in at least central portions of the condylar head 22 achieves a high contact area in the FIGS. 1 and 2 orientation that corresponds to a condition of maximum loading. Pivoting movement about a medial to lateral axis is permitted in this position. Additionally, from this position, an anterior to posterior translation of the condylar head 22 is permitted along the planar section 56 of the inferior bearing surface 52. Still further, the tapered configuration of the condylar head 22 generated by rotating the flat curve about the medial-lateral axis and the medial to lateral linear configuration of the bearing surface 50 permits a slight pivoting about superior to inferior axis, while still achieving a substantially line contact.

In addition to the enhanced performance achieved by the above-described shapes of the bearing surface 52 and the condylar head 22, the preferred plasma-sprayed double screws with the anti-micromovement lock prevents micromovement of either component of the prosthesis 10 that could affect the alignment of the respective bearing surfaces and that could generate deterioration of the bone to which the respective components of the prosthesis 10 are affixed. Furthermore, the plastic bearing 26 is securely fixed to the metallic bone attachment portion 24 and provides a relatively thick bearing component that will last longer in response to the frequent forces imposed during normal usage of the joint. Additionally, the sliding locked engagement of the bearing 26 in the bone attachment portion 24 can be separated to correct wear or damage to the bearing that may occur or to address any changing needs of the patient.

What is claimed is:

1. A temporomandibular prosthetic joint comprising:
   a metallic condyle component having an elongate ramus attachment portion with opposed superior and inferior ends and bone attachment means intermediate said ends, a generally condylar head disposed at said superior end of said ramus attachment portion, said condylar head being a surface of revolution defined by rotating a curve about a medial-to-lateral axis and having opposed medial and lateral ends, portions of said head in proximity to said medial and lateral ends being tapered toward the medial-to-lateral axis of the condylar head;
   a fossa component having a metallic bone attachment member and a bearing member formed from a non-metallic material, said bearing member having an inferior bearing surface in articular and sliding bearing engagement with said condylar head, said bearing surface being configured to permit a major articulation of said condyle component about a medial-to-lateral axis, a minor articulation of said condyle component about an anterior-to-posterior axis and translation of said condylar head on said bearing surface in a substantially anterior-to-posterior direction.

2. The temporomandibular prosthetic joint of claim 1, wherein the condyle component and the fossa component have relative positions and alignments corresponding to a maximum load therebetween, said bearing surface of said fossa component being configured for exhibiting greatest congruency with said condylar head in said position corresponding to said maximum load.

3. The temporomandibular prosthetic joint of claim 2, wherein said inferior bearing surface of said fossa component includes a substantially arcuate concavity at said position corresponding to said maximum load, said arcuate concavity being configured for substantially congruently conforming to portions of said condylar head centrally between the respective medial and lateral ends of the condylar head.

4. The temporomandibular prosthetic joint of claim 3, wherein said inferior bearing surface of said fossa component includes a substantially planar section tangent to said arcuate concavity and extending substantially anteriorly therefrom for accommodating anterior-to-posterior translation of said condylar head along said inferior bearing surface of said fossa component.

5. The temporomandibular prosthetic joint of claim 4, wherein the bearing member includes an anterior lip projecting inferiorly from the bearing member substantially at an anterior portion of said planar bearing section, said anterior lip being disposed for limiting anterior movement of said condylar head on said bearing member and preventing dislocation therebetween.

6. The temporomandibular prosthetic joint of claim 5, wherein said inferior bearing surface is substantially linear in medial-to-lateral directions at all locations thereon, said linear configuration of said inferior bearing surface in medial to lateral directions permitting controlled pivoting at tapered portions of said condylar head about a medial-to-lateral axis.

7. The temporomandibular prosthetic joint of claim 6, further comprising a posterior wall extending substantially inferiorly and tangentially from a posterior end of said arcuate concavity for substantially preventing posterior movement of said condylar head from said arcuate concavity area corresponding to maximum load.

8. The temporomandibular prosthetic joint of claim 1, wherein said inferior bearing surface is substantially linear in medial-to-lateral directions at all locations thereon, said linear configuration of said inferior bearing surface in medial to lateral directions permitting controlled pivoting of said condylar head about a medial-to-lateral axis.

9. The temporomandibular prosthetic joint of claim 1, wherein said metallic bone attachment member of said fossa component includes a superior wall having a dovetail section extending substantially in a medial-to-lateral direction, said bearing member of said fossa component including a superior wall with a mating dovetail member extending in a medial-to-lateral direction for sliding engagement with the dovetailed section of the metallic bone attachment member, said metallic bone attachment member and said bearing member further including locking structure for locking said bearing member and said metallic bone attachment member in a selected medial-to-lateral position.

10. The temporomandibular prosthetic joint of claim 9, wherein said superior wall of said metallic bone attachment member of said fossa component has an inferior surface, said dovetail member of said metallic bone attachment portion being formed on said inferior surface, said superior wall of said bearing member having a superior surface, said mating dovetailed section being formed on said superior surface.

11. The temporomandibular prosthetic joint of claim 10, wherein the metallic bone attachment member of said fossa component further includes a posterior support wall extending form said inferior surface, and having said dovetailed member, said bearing member further having a posterior wall in bearing engagement with said posterior wall of said metallic bone attachment member.

12. The temporomandibular prosthetic joint of claim 11, wherein the locking means are formed on facing surfaces of the posterior walls of the metallic bone attachment member and the bearing member.

13. The temporomandibular prosthetic joint of claim 12, wherein the attachment means comprise a groove formed in the posterior wall of the metallic bone attachment portion and a deflectable ridge formed on the posterior wall of the bearing member.

14. The temporomandibular prosthetic joint of claim 1, wherein the bone attachment means comprise double lock screws, each said double lock screw having an outer screw with internal and external threads and a plurality of longitudinal slits, each said double screw further comprising an inner screw threadedly engageable with the internal threads of the outer screw for deflecting portions of the outer screw outwardly for locking engagement with adjacent portions of said prosthetic joint and with portions of bone adjacent thereto.

15. A temporomandibular prosthetic joint comprising:
a metallic condyle component having an elongate ramus attachment portion with opposed superior and inferior ends and bone attachment means intermediate said ends, a condylar head disposed at said superior end of said ramus attachment portion, said head being a surface of revolution defined by rotating a curve about a medial-to-lateral axis and having opposed medial and lateral ends, portions of said head in proximity to said medial and lateral ends being tapered toward the medial-to-lateral axis of the condylar head; and
a fossa component having a metallic bone attachment member with a superior wall and a posterior wall extending from said superior support wall, said superior wall having an inferior surface, and said posterior support wall having an anterior surface, a bearing member formed from a high molecular weight polyethylene, said bearing member having a superior wall with a superior surface engaged with the inferior surface of the superior wall of the bone attachment member, said bearing member further having a posterior wall with a posterior surface engaging the anterior surface of the posterior wall of the bone attachment member, said bearing member further including a substantially concave inferior bearing surface facing away from said bone attachment member for articular and sliding bearing engagement with said condylar head, said inferior bearing surface of said bearing member including generally cylindrically concave section formed by portions of said inferior and posterior walls of said bearing member and being substantially congruent with portions of said condylar head between said medial and lateral ends, said inferior bearing surface further comprising a substantially planar section extending generally anteriorly and tangently from said cylindrically concave region for permitting sliding movement of said condylar head in a substantially anterior-to-posterior direction on said bearing member.

16. The temporomandibular prosthetic joint of claim 15, wherein the bearing member further comprises and anterior lip projecting inferiorly at an anterior extreme position on said bearing member for limiting anterior sliding movement of said condylar head along said bearing member.

17. The temporomandibular prosthetic joint of claim 16, wherein said inferior surface region of said bearing member is substantially linear in medial-to-lateral directions at all locations thereon.

* * * * *